United States Patent [19]

Fox

[11] 4,342,218
[45] Aug. 3, 1982

[54] METHOD AND APPARATUS FOR ZEROING AND CALIBRATING AN INVASIVE BLOOD PRESSURE MONITORING SYSTEM

[76] Inventor: Forrest Fox, 5607 Jackwood, Houston, Tex. 77096

[21] Appl. No.: 112,430

[22] Filed: Jan. 16, 1980

[51] Int. Cl.³ .............................................. G01L 27/00
[52] U.S. Cl. ..................................... 73/4 R; 128/673
[58] Field of Search ................. 73/4 R, 756; 128/672, 128/673, 674, 675

[56] References Cited

U.S. PATENT DOCUMENTS

| | | | |
|---|---|---|---|
| 2,600,324 | 6/1952 | Rappaport | 73/4 R |
| 3,435,819 | 4/1969 | Reynolds | 128/674 |
| 3,495,585 | 2/1970 | Halligan | 128/674 |
| 3,581,733 | 6/1971 | Grandjean | 128/673 |
| 3,996,927 | 12/1976 | Frank | 128/673 |

*Primary Examiner*—S. Clement Swisher
*Attorney, Agent, or Firm*—Bernard A. Reiter

[57] ABSTRACT

A method and apparatus for zeroing and calibrating an invasive blood pressure monitoring system includes a method whereby the diaphragm of a strain gauge type blood pressure transducer may be subjected to a zero reference pressure for zeroing and an elevated pressure for calibration of a blood pressure monitoring system in order that an oscilloscope display of the blood pressure waveform of the patient may be accurately monitored by visual inspection of an oscilloscope screen. During zeroing and calibration of the blood pressure monitoring system, the invasive interconnection with the bloodstream of the patient is ensured to be closed to prevent the occurrence of air embolus and the blood pressure transducer system is also isolated from the atmosphere at all times to prevent invasion of the system by means of bacteria.

26 Claims, 8 Drawing Figures

METHOD AND APPARATUS FOR ZEROING AND CALIBRATING AN INVASIVE BLOOD PRESSURE MONITORING SYSTEM

FIELD OF THE INVENTION

This invention relates generally to the measuring of blood pressure in a patient and particularly to blood pressure measurement of the invasive type where blodd pressure is measured directly from the cardiovascular system of the patient. Even more particularly, the present invention is directed to a method and apparatus for zeroing and calibrating invasive blood pressure monitoring systems in order to ensure the accuracy of blood pressure information to be displayed by means of an oscilloscope or other display or recording device. This invention may also be used for zeroing and calibrating of pressure monitoring systems for the measurement of physiologic fluid system pressures other than blood pressure, such as intracranial pressure, intraoccular pressure, intrauterine pressure, etc.

BACKGROUND OF THE INVENTION

Measurement of the blood pressure of a patient historically has been accomplished by means of a noninvasive system whereby the cardiovascular system of the patient does not become invaded in any manner whatever and contamination of the cardiovascular system is not possible. Typically, an inflatable cuff is placed about the patient's upper arm and is inflated sufficiently to close off the underlying brachial artery. Upon slowly releasing pressure from the cuff while watching the pressure gauge or mercury manometer interconnected with the cuff, and listening with a stethoscope placed over the brachial artery distal to the cuff, the pressure at which the Korotkoff sounds appear and disappear are determined and these pressures are the patient's systolic and diastolic pressures, respectively. This method is known as the auscultatory method of indirect or noninvasive measurement of blood pressure. In general, the cuff may be placed around other appendages and inflated to a pressure above systolic pressure and other techniques such as palpation, oscillometry or ultrasound may be used to detect the patient's systolic, diastolic or mean pressure as the cuff pressure is slowly reduced. Intermittent monitoring of blood pressure may be accomplished by means of noninvasive blood pressure measurement systems but in recent times, especially in conjunction with surgical procedures where accurate and continuous pressure monitoring is highly desirable, it has become the practice to achieve continuous monitoring of blood pressure by means of an invasive blood pressure monitoring system wherein an artery of the patient is cannulized and blood pressure is detected and displayed or recorded by means of a blood pressure strain gauge, which is also referred to as a blood pressure transducer. This same technique of direct or invasive blood pressure monitoring may also be used to measure the blood pressure, which cannot be measured by noninvasive methods, at other sites in the cardiovascular system than in the arterial system. For example, the blood pressure in the venous system, the pulmonary vascular system and the chambers of the heart may be measured with this invasive technique. Furthermore, it is a common practice now to use this invasive technique to simultaneously measure several of these pressures in patients during surgery and in intensive care units. In practice, the pressure of the blood of the cardiovasular system of the patient is transmitted to a diaphragm of a strain gauge, through a fluid column, thus causing yielding of the diaphragm in accordance with the blood pressure of the patient. Yielding of the diaphragm is detected by means of an electrical system that develops an electrical signal that is directly proportional to the amount of strain that results from deflection of the transducer diaphragm. This electrical signal is amplified and otherwise conditioned and transmitted to the input of an oscilloscope and is displayed as a waveform on the screen of the oscilloscope. This amplified and conditioned electrical signal may also be transmitted to the input of various types of recorders or other display devices, such an analog meters or digital displays. Throughout the rest of this application, the oscilloscope will be cited as a typical display or recording device and the amplifier and signal conditioners will be considered to be part of the oscilloscope.

In order for the oscilloscope to properly display the waveform signal being emitted from the transducer, the transducer electrical signal must be zeroed with respect to a base line representing zero or atmospheric pressure on the oscilloscope. To accomplish zeroing of the blood pressure transducer electrical signal, atmospheric pressure, or some other zero reference pressure, must be communicated to the diaphragm of the transducer. The diaphragm, being at the zero reference pressure, will emit an electrical signal representing the zero reference pressure and this pressure signal will appear on the oscilloscope in visual form. The oscilloscope is then adjusted to bring the zero reference pressure signal into registry with a base line representing zero or atmospheric pressure on the screen of the oscilloscope. After this has been done, the blood pressure monitoring system is then considered to be zeroed.

After zeroing of the blood pressure monitoring system, it is then necessary to check the calibration of the blood pressure monitoring system, thus ensuring that the transducer and oscilloscope are capable of proper electrical signals within the pressure range that is expected. The typical method for calibration of the blood pressure monitoring system is to interconnect the transducer either directly or through a system of valves and tubing with the output hose of a mercury manometer and to pump the manometer up to the maximum expected pressure above the zero reference pressure, for example, 250 millimeters of mercury. With the blood pressure transducer thus connected and a pressure of 250 millimeters of mercury above the zero reference pressure applied to the diaphragm of the transducer, the transducer will be emitting an electrical signal representing a pressure of 250 millimeters of mercury above the zero reference pressure. This signal is transmitted to the oscilloscope screen for visual display and, if the blood pressure transducer and oscilloscope are properly calibrated, will provide a visual reading of 250 millimeters of mercury. Thus, the blood pressure transducer is subjected to a known pressure above the zero reference pressure, i.e. 250 millimeters of mercury, and this known pressure is visually inspected on the oscilloscope screen. If the pressure on the oscilloscope screen reads other than 250 millimeters of mercury, then the blood pressure monitoring system must be adjusted to obtain a reading of 250 millimeters of mercury. If the blood pressure monitoring system is of the type which cannot be adjusted or if it is not possible to adjust it to obtain a reading of 250 millimeters of mercury, then the blood pressure monitoring system is defective and must not be used to monitor patients' pressure until the defect is isolated and corrected. The defect may be in the transducer or oscilloscope or both.

Although zeroing and calibrating of invasive blood pressure monitoring systems is quite simple, there are serious problems associated with typical methods of accomplishing zeroing and calibrating. The fluid column connecting the cardiovascular system of the patient to the transducer diaphragm should remain closed and sterile. However, opening the blood pressure monitoring system to atmospheric pressure for zeroing allows bacteria and other contaminants to enter the fluid column that is interconnected with the cardiovascular system of the patient. When this occurs, it is possible for bacteria to migrate through the fluid system to the cardiovascular system of the patient and cause bacterial infection thereof and thus endanger the health of the patient. It is also possible in normal use that this fluid which has been contaminated will be infused into the patient, endangering the health of patient. Further, when mercury manometers, such as are typically mounted on the walls of hospital facilities, are interconnected with the blood pressure monitoring system for calibration, the manometer is not in sterile condition. It is possible, therefore, for bacteria and other contaminants to be injected into the fluid of the blood pressure monitoring system, and these bacteria may migrate to the cardiovascular system of the patient or the contaminated fluid may, in normal use, be infused into the cardiovascular system of the patient. It is desirable, therefore, to provide a method and apparatus for invasive blood pressure monitoring wherein the system is maintained in a closed condition at all times with respect to the bacteria-containing external environment, and thus, the possibility of introducing bacteria and other contaminants into the cardiovascular system of the patient is avoided.

When an invasive blood pressure monitoring system is interconnected with the cardiovascular system of a patient and a transducer zeroing and calibrating operation is in progress, a valve in the tubing leading from the cannula to the transducer must be closed. During zeroing, if the valve or stopcock is left open, the arterial pressure of the patient will pump the patient's blood through the tubing and out of the orifice which has been opened to atmospheric pressure for zeroing. The results will be loss of blood which in the most severe case could lead to exsanguination of the patient. During calibration of the blood pressure monitoring system, the diaphragm within the transducer dome will be subjected to a pressure which typically exceeds the blood pressure of the patient. If the above-referenced stopcock in the tubing to the patient is open during attempted calibration, air will be injected through the tubing to the patient and air embolus will result.

In order to avoid the previous hazards of contamination and air embolus which may result during the calibration of an invasive blood pressure monitoring system, the system is sometimes simply zeroed but not calibrated. The result of this omission can be very serious. For example, if the pressure monitoring system is not properly calibrated, the physician may believe the patient's blood pressure is high when in reality it is low. The physician would then, in all probability, inject a medicament to lower the patient's blood pressure. Inappropriate administration of such a medicament could cause the patient to go into shock or cardiac arrest. Conversely, if the physician is falsely led to believe the patient's blood pressure is low when in reality it is high, the physician would then, in all probability, inject a medicament to raise the patient's blood pressure. Inappropriate administration of such a medicament could cause the patient to experience a stroke. Other possible harmful consequences of inaccurate invasive blood pressure measurements include inappropriate infusion of fluid causing heart failure, performing unnecessary surgery or failing to perform necessary surgery. This possibility of causing a physician to inappropriately prescribe for or treat a patient thus leading to a worsening of the patient's condition is considered to be the most serious problem associated with invasive blood pressure monitoring.

At the time of the initiation of use of an invasive blood pressure monitoring system, it is necessary that the site of the fluid-air interface at which the system is opened to atmosphere to establish the zero reference pressure be leveled with respect to the right atrium of the patient's heart, which is typically the mid-thoracic level when the patient is supine. This leveling ensures that the transducer senses only blood pressure and not a hydrostatic pressure caused by a difference in height between the fluid-air interface and the patient's heart, as well. Because there is no convenient, accurate process available by which to ensure that the fluidair interface is in proper alignment with the patient's heart, often the leveling is accomplished by simple line of sight over a distance of several feet. This process can be dangerous to the patient by causing inaccurate pressure measurement, especially when the blood pressure measured is expected to be quite low. For example, the normal range for pulmonary wedge pressure to 6 to 12 millimeters of mercury, and each centimeter of leveling error will result in the addition to or subtraction from the blood pressure measurement of a hydrostatic pressure equal to $\frac{3}{4}$ millimeter of mercury. Therefore, a leveling error of only four centimeters will cause a measurement error of 25%–50% of the actual pressure. It is desirable, therefore, to provide a convenient means for positively ensuring accurate leveling of the fluid-air interface with respect to the mid-thoracic line of the patient and thus ensure elimination of any pressure measurement error due to misalignment of the fluid-air interface with the patient's heart.

Blood pressure transducers are typically of quite expensive nature, in the order of $400 to $500, and being of delicate nature, are quite easily damaged due to movement of personnel about the patient during a surgical procedure or in an intensive care unit. Many manufacturers of blood pressure transducers provide quality holders for the transducers themselves and thus provide the transducers with adequate protection, but, provision is not made in these holders for other devices that are commonly employed in conjunction with blood pressure transducers. For example, constant flush systems are often employed in conjunction with blood pressure transducers to ensure against coagulation of the patient's blood at the cannula insertion site, which might otherwise result in blockage of the blood pressure monitoring system and thus inaccurate blood pressure measurement. Typical continuous flush systems are interconnected with the blood pressure transducers and extend therefrom in an unprotected position where they are often struck and broken by personnel attending the patient. It is possible, also, that application of inadvertent force to a continuous flush device or the plumbing interconnected therewith will result in damage to the blood pressure transducer. Moreover, breakage of the continuous flush device or its plumbing can result in contamination of the cardiovascular system of the patient. With rapid worldwide acceptance of invasive cardiovascular hemodynamic monitoring, there is a need for a special holder to hold one or more continuous flush systems and transducers to prevent damage thereto; level the fluid-air interface with the midthoracic line of the patient; and house a system that provides a closed sterile path with bacteria filtering in order to prevent contamination while zeroing and calibrating the pressure monitoring system.

In view of the foregoing, it is a primary feature of the present invention to provide a novel method and apparatus for accomplishing zeroing and calibrating of blood pressure monitoring systems without in any way endangering the patient from the standpoint of bacterial contaimination, loss of blood or inappropriate administration of medicaments or other inappropriate treatment based on inaccurate pressure measurements due to reluctance to calibrate the pressure monitoring system for fear of contamination thereof.

It is also a feature of this invention to provide a novel system for invasive monitoring of the blood pressure of patients wherein positive alignment of the fluid-air interface used to establish the zero reference pressure with the mid-thoracic line of the patient may be achieved simply and efficiently, thereby preventing erroneous blood pressure readings that might otherwise occur due to improper leveling.

It is an even further feature of this invention to provide a novel apparatus for holding and protecting one or more pressure transducers of like or different designs and the continuous flush systems and other plumbing attached thereto to prevent breakage of the transducers, continuous flush systems or plumbing which might result in costly loss of equipment, inaccurate pressure measurement or contamination of the cardiovascular system of the patient.

It is also a feature of this invention to provide a novel system for zeroing and calibrating of a plurality of blood pressure monitoring systems, each consisting of a blood pressure transducer and oscilloscope trace or other display device, used simultaneously for one patient, wherein a single zeroing and calibrating mechanism may be utilized for selectively zeroing and calibrating each blood pressure monitoring system, while maintaining each of the systems in an environmentally closed condition during the zeroing and calibrating procedure. Furthermore, all such blood pressure monitoring systems interconnected with one zeroing and calibrating mechanism may be zeroed and calibrated simultaneously thereby assuring identical, superimposed trace deflections on the oscilloscope in response to the calibrating pressure.

It is also a feature of this invention that if a plurality of pressure transducers of different designs are supported and protected in one holder and interconnected with a single zeroing and calibrating mechanism, all transducer types need not be held with the sensing diaphragm at the same height in order for the pressure monitoring system to indicate accurate pressure measurements without errors introduced by hydrostatic pressure differences.

Other and further objects, advantages and features of the invention will become obvious to one skilled in the art upon an understanding of the illustrative embodiment about to be described and various advantages, not referred to herein, will occur to one skilled in the art upon employment of the invention in practice.

SUMMARY OF THE INVENTION

The present invention is directed to the provision of a method and apparatus for zeroing and calibrating, either singly or in plural interconnection, blood pressure monitoring systems wherein each blood pressure measurement system remains closed to the external environment at all times. A transducer support table is provided which is adapted for interconnection with the vertical pole of any I. V. stand and which is also adapted to receive one or more transducer support inserts. Each of the transducer support inserts is specifically adapted to support a particular type of blood pressure transducer and is also adapted to provide structural support for a continuous flush system such as is typically employed in conjunction with blood pressure transducers, thus providing adequate protective support for both the blood pressure transducer and the continuous flow system to prevent damage thereto by personnel and equipment moving about the patient. The transducer support table is also provided with a calibration support structure that is adapted to support a calibration chamber. The transducer support table also includes a leveling structure to ensure accurate leveling of the fluid-air interface in the calibration chamber with respect to the mid-thoracic line of the patient, thus ensuring that no hydrostatically induced pressure differential is developed due to inaccurate leveling.

The support table structure functions as a receiver for selected transducer support inserts, each insert being adapted to receive a selected type of transducer for protective support thereof. Each of the support inserts is also provided with a support cradle that is adapted to provide support for transducer connection plumbing that extends from the transducer to the cardiovascular system of the patient. Under circumstances where a continuous flush system is employed in conjunction with the transducer for the purpose of preventing coagulation of blood which might otherwise interfere with accurate monitoring of the patient's blood pressure, the support cradle structure also provides protective structural support for the continuous flush device. Each of the transducer support inserts is designed to simultaneously provide adequate support and protection for the transducer and the continuous flush system. The support table structure is also provided with a support that properly positions a blood pressure calibration chamber in accurately leveled relation with respect to the leveling structure facilitating zeroing and calibrating of the pressure monitoring system.

The method and apparatus according to this invention effectively provides a system for zeroing and calibrating of a blood pressure monitoring system without any risk of bacterial contamination to the cardiovascular system of the patient. A three-position selector valve having three ports is provided which, in each of its three positions, interconnects two of the three ports and simultaneously blocks interconnection of the third port with these two. In one position, the selector valve interconnects the blood pressure transducer which is connected to one port of the valve with the fluid filled tubing that is connected to a second port of the valve and that extends to the cardiovascular system of the patient, thus allowing the blood pressure transducer to sense the blood pressure of the patient. In the second position of the selector valve, interconnection between the transducer and the patient is cut off and interconnection between the transducer and the calibration chamber, which is connected to the third port of the valve, is established. Thus, with the selector valve in the blood pressure monitoring position, interconnecting the transducer with the cardiovascular system of the patient, atmospheric pressure for zeroing and elevated pressure for calibration cannot be transmitted to the patient through the calibration chamber. In the second position of the selector valve, the transducer can be zeroed and calibrated by communication of respective pressures through the calibration chamber. With the valve in this position, there is no possibility of inadvertent loss of blood from the patient or transmission of air embolus to the patient.

Communication of external pressures such as atmospheric pressure and pressure from a mercury manometer through the calibration chamber into the blood pressure monitoring system is allowed only with communication through a bacteria filter that functions to prevent contamination of the system during zeroing and calibrating. Thus, the blood pressure monitoring system always remains closed with respect to bacteria and other contaminants from the external environment. A mercury manometer may be interconnected with the system for the purpose of accomplishing calibration and, even though the manometer is unsterile, the bacteria filter will maintain the sterile condition of the system while allowing transmission of calibration pressure therethrough.

In the third position of the selector valve interconnection between the calibration chamber and the fluid filled tubing that extends to the cardiovascular system of the patient is established. However, between the selector valve and the patient there is another valve of the same design. The third port of this second valve is connected to a reservoir of sterile fluid used to prime the tubing system, transducer diaphragm chamber and calibration chamber. If the first selector valve is set in this third position, the second selector valve is set in the position to interconnect the calibration chamber with the fluid reservoir and thus block connection of the patient's cardiovascular system with the calibration chamber. If the first selector valve is inadvertently set in the third position, instead of the second position, for zeroing and calibrating while the system is connected to the patient, there are still safeguards to protect the patient from loss of blood or air embolus. If the first selector valve is placed in the third position while the system is connected to the patient and there is no pressure applied to the calibration chamber, such as during zeroing, the patient's blood pressure will pump some of the patient's blood from the patient's cardiovascular system into the tubing, raising the level of fluid in the calibration chamber only until the fluid reaches the bacteria filter. It is a beneficial characteristic of the bacteria filter that fluid will not pass through it at physiologic pressures. Therefore, only an insignificantly small amount of blood, approximately four milliliters, leaves the patient's cardiovascular system into the tubing. Furthermore, this small amount of blood will not be contaminated and can be reinfused into the patient as soon as the error is observed. It is also a beneficial characteristic of the bacteria filter that, by forcing air through the filter which moves the fluid away from contact with the filter and restores the proper fluid level in the calibration chamber, the filter is immediately completely restored to its original condition and continues to function as an effective barrier to the transmission of bacteria into the system. If, on the other hand, the first selector valve is set in the third position while the system is connected to the patient and a calibrating pressure is applied to the calibration chamber through the bacteria filter, the infusion of air emboli is not absolutely prevented but it is highly unlikely. Proper technique requires zeroing of the pressure monitoring system before calibrating. If this error in positioning the first valve were made, it would probably be discovered and corrected while zeroing. However, even if it were not corrected while zeroing, the error would immediately be indicated while calibratng because the manometer used to calibrate would be incapable of maintaining a pressure, applying pressure to the calibration chamber would cause no deflection on the oscilloscope, and the fluid level in the calibration chamber would begin to drop. These indications, plus the fact that all the fluid from the calibration chamber and connecting tubing would first have to be infused into the patient ahead of air, would allow adequate time to correct the error before air would be infused.

BRIEF DESCRIPTION OF THE DRAWINGS

In order that the manner in which the above-recited advantages and objects of the invention are attained, as well as others, which will become apparent, can be understood in detail, more particular description of the invention, briefly summarized above, may be had by reference to the specific embodiments thereof that are illustrated in the appended drawings, which drawings form a part of this specification. It is to be understood, however, that the appended drawings illustrate only typical embodiments of the invention and therefore are not to be considered limiting of its scope, for the invention may admit to other equally effective embodiments.

In the Drawings.

DESCRIPTION OF PREFERRED EMBODIMENT

Figure 1:
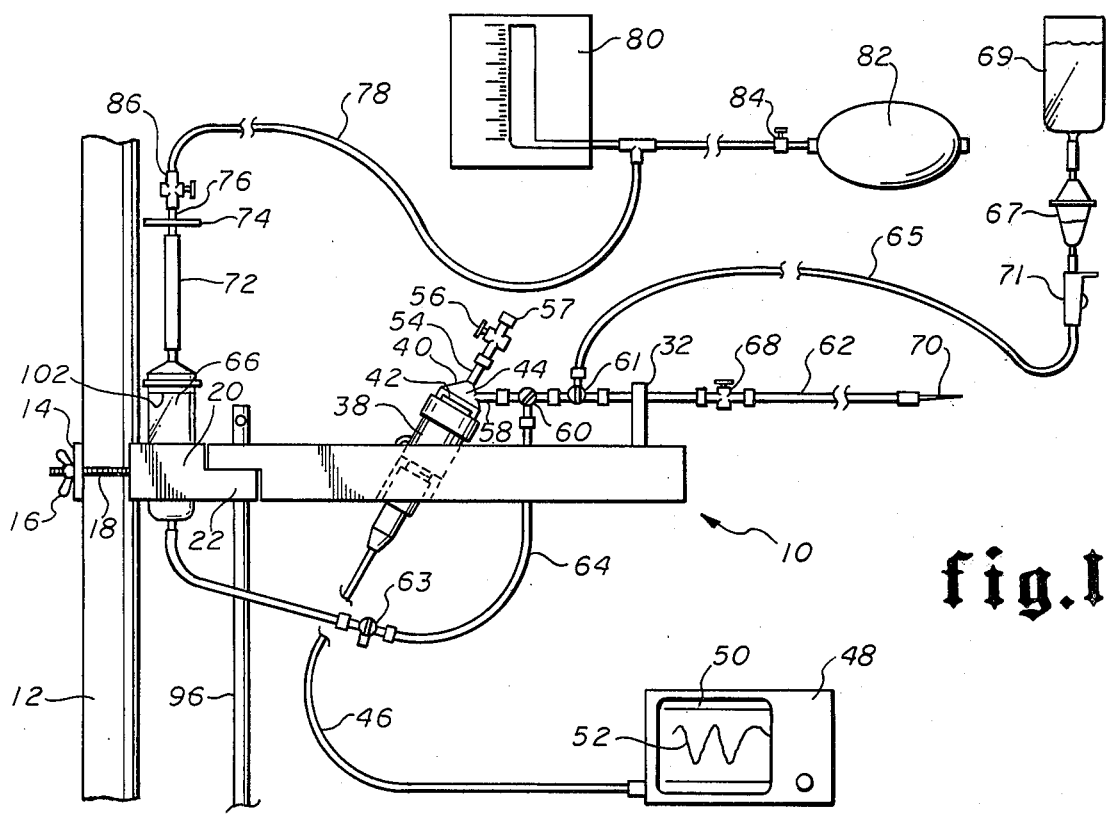
FIG. 1 is a side elevational view of a transducer support structure having a blood pressure transducer supported therein and providing a schematic illustration of a system for zeroing and calibrating of the pressure monitoring system while maintaining the system closed and sterile with respect to bacteria and contaminants in the external environment.
Figure 4:
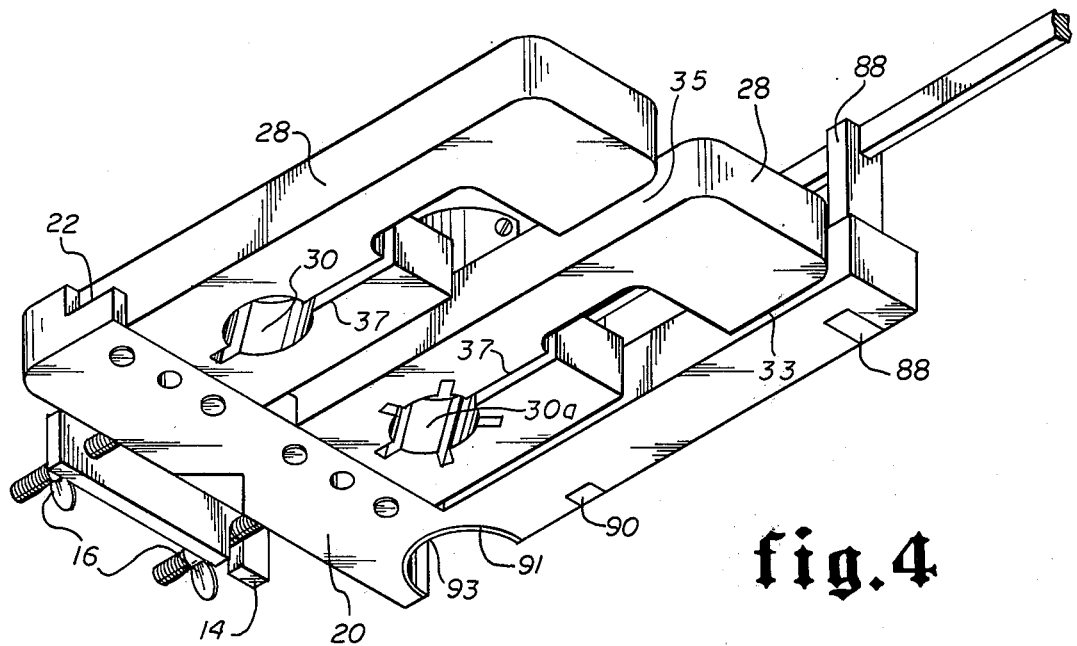
FIG. 4 is an isometric view of the transducer support table structure of FIG. 3, the view illustrating the bottom and side portions of the transducer support table and transducer support inserts.
Figure 3:
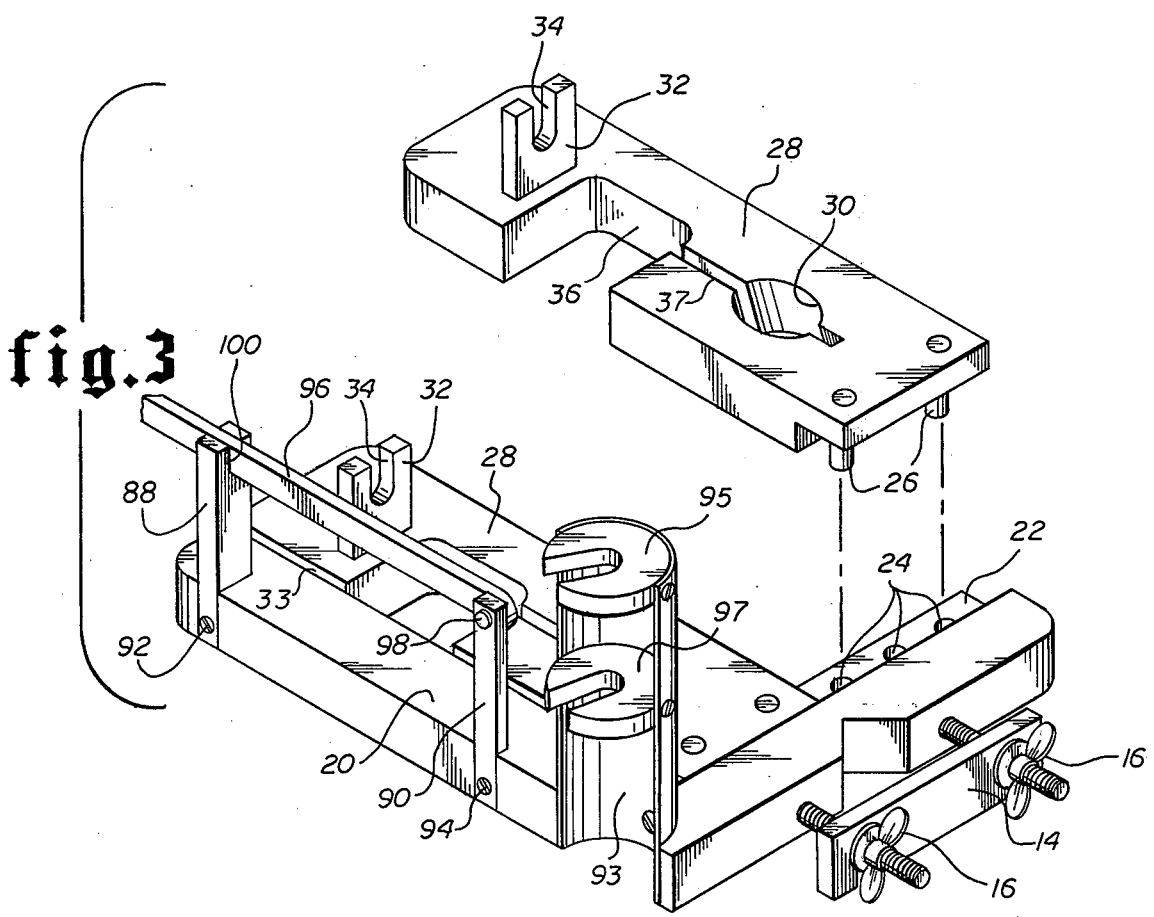
FIG. 3 is an isometric view of the transducer support table structure of this invention with two transducer support inserts, one being shown in separated relation with the transducer support table structure.

Referring now to the drawings and first to FIG. 1, a transducer support table structure manufactured in accordance with this invention is illustrated generally at 10 and which is shown to be connected to an I. V. pole 12 by means of a clamp bar 14 that is tightened in position on the I. V. pole by wing nuts 16 that are received by threaded elements 18. The transducer support table structure is generally in the form of an L-shaped, rigid body member 20 which is best illustrated in FIGS. 3 and 4. The body member 20 is formed to define a transducer insert support ledge 22 having a plurality of apertures 24 formed therein that are adapted to receive connector pins 26 of a transducer support insert 28. The transducer support ledge 22 is of sufficient width that it can receive one or more transducer support inserts 28, thereby allowing the transducer support table structure 20 to provide protective support for a plurality of transducers and other plumbing structures interconnected therewith. Blood pressure transducers for invasive cardiovascular hemodynamic monitoring are manufactured by several different manufacturers in several different forms. Each of the support insert adaptors 28 is formed to define a transducer receptacle or aperture 30 of a particular configuration mating with the external configuration of a respective one of the various available transducers. As shown in FIG. 4, each of the transducer support inserts 28 are formed to define transducer receptacles 30 and 30a of different configuration, conforming to the particular configuration of the transducer to be received thereby. Each of the transducer support insert adaptors 28 is also provided with a protective supporting cradle 32 projecting upwardly therefrom and being formed to define a recess or groove 34 within which a portion of the transducer plumbing is received and provided with protective support. The transducer support insert adaptors are also formed to define a recess 36 that allows a T-fitting or valve to depend downwardly from the plumbing of the transducer in the manner shown in FIG. 1 without interference by the transducer support insert structure. The apertures 24 of the transducer insert support ledge 22 and the connector pins 26 of the transducer support insert 28 are so located and the transducer inserts are so formed as to form channels 33 and 35, respectively, between the transducer support body 20 and the adjacent transducer support insert and between adjacent transducer support inserts. The transducer support inserts are also formed to define a channel 37 between the recess 36 and the transducer receptacle 30. The clamp bar 14 is slotted in such a way as shown in FIG. 4 that the clamp bar may be lifted off one of the threaded elements 18 and pivoted on the other threaded element. In this way the transducer support table may be attached to an I. V. pole without removing the wing nuts 16. All blood pressure transducers have an electrical cable 46 as shown in FIG. 1 attached thereto which is terminated in a connector which is larger than the transducer receptacle. In order to locate the transducer body 38 in the transducer receptacle 30, the electrical cable may be passed through channel 33 or 35 into the recess 36 and then through channel 37 into the transducer receptacle 30, thereby allowing the transducer body 38 to be placed into the transducer receptacle 30.

Most blood pressure transducers incorporate a body structure 38 of generally cylindrical form as illustrated in FIG. 1 with a transducer dome 40 being interconnectable with the body structure and providing a protective enclosure for the sensitive diaphragm 42 of the transducer. The transducer dome also provides a sealed chamber 44 within which the patient's blood pressure is transmitted to the transducer diaphragm during the monitoring operation. During zeroing, atmospheric or a zero reference pressure is communicated to the diaphragm chamber 44 and during calibration, a preselected elevated pressure above atmospheric or zero reference pressure is transmitted to the diaphragm chamber in order to determine if the pressure monitoring system is properly calibrated. Blood pressure transducers are provided with electrical output conductors 46 that are interconnectable with an oscilloscope 48, thereby causing the screen 50 of the oscilloscope to display a waveform 52 representing the blood pressure of the patient.

Virtually all transducer domes are formed to define a central or upper connector 54 that is controlled by means of a stopcock 56 and a side connector 58 that is also valve controlled. The stopcock 56 is of the on/off or two-way type, the end of which is covered by a cap 57. In accordance with the present invention, a selector valve 60, which is of the three-way type previously described, is interconnected with the side outlet 58 of the transducer dome and functions to establish selective connection of the diaphragm chamber 44 through three-way valve 61 with a blood pressure tube 62 or a zeroing and calibrating tube 64 that is interconnected through a three-way valve 63 with a calibration chamber 66. The blood pressure tube 62 is also provided with a two-way stopcock 68 and that tube extends to a cannula 70 that is introduced into the cardiovascular system of the patient. Where a single arterial blood pressure reading is taken, the cannula 70 is commonly inserted into the radial artery of the patient's arm but other pressures of the cardiovascular system of the patient may be monitored as well simply by appropriate location of the cannula in various arteries and veins of the patient.

The calibration chamber 66 is provided with an upper connector element 72 to which is interconnected a bacteria filter 74. The filter 74 has an inlet connection 76 at the upper portion thereof which is adapted to receive the three-way vent valve 86 which is connected to the pressure tube 78 of a mercury manometer 80 that is energized by means of a controllable pump bulb 82 and control valve 84. The vent valve 86 is included in the manometer tube 78 in order that atmospheric pressure may be introduced into the calibration chamber 66 across the bacteria filter 74 without venting the pressure in the manometer 80 and pressure tube 78. The three-way valve 61 is interconnected through tubing 65 to a drip chamber 67. The drip chamber 67 is connected to a reservoir 69 of sterile fluid which is used to prime the system. A roller clamp valve 71 located on tubing 65 between the drip chamber 67 and the three-way valve 61 may be used to squeeze the tube 65 to prevent flow.

Figure 5:
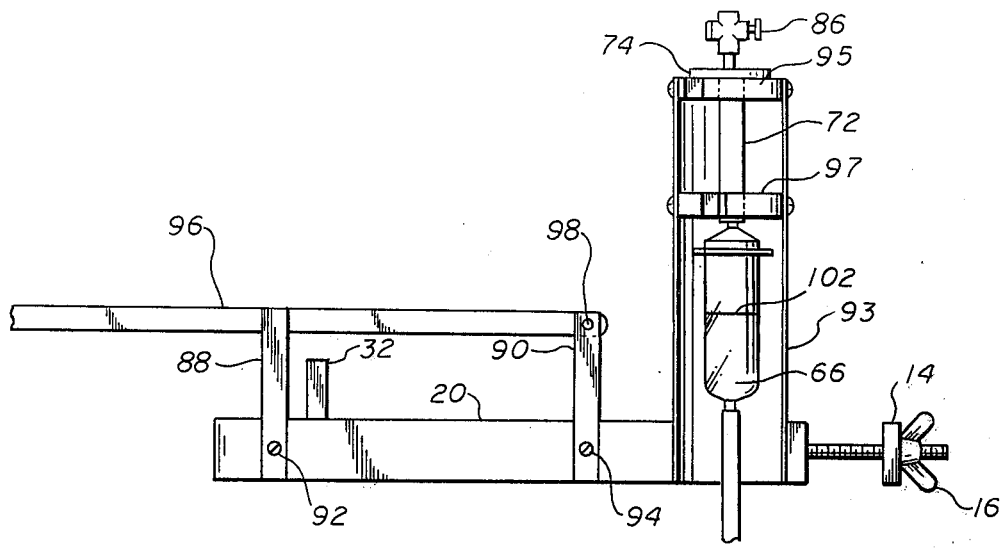
FIG. 5 is an end view of the transducer support structure of FIGS. 3 and 4 illustrating the position of a calibration chamber in assembly therewith.

In order to eliminate any pressure measurement error which would be caused by a difference in level between the fluid-air interface in the calibration chamber and the patient's mid-thoracic line, it is necessary that the transducer support table 20 be adjusted with respect to the I. V. pole 12 so as to position the fluid-air interface in the calibration chamber in accurately leveled relationship with the mid-thoracic line of the patient. This activity may be referred to as leveling of the transducer support. As shown particularly in FIG. 3, a pair of level arm support posts 88 and 90 are interconnected with the transducer support table 20 by means of bolts or screws 92 and 94. A leveling arm 96 is interconnected by means of a pivot 98 to the upper portion of the support post 90 and is adapted to be received within a slot 100 defined in the upper portion of support post 88. Ordinarily, the leveling arm 96 is pivoted downwardly and merely hangs on the pivot 98 in substantially parallel relation with the I. V. pole 12, in which position it does not interfere in any way with operations in conjunction with blood pressure monitoring. To accomplish leveling of the transducer support table 20, the leveling arm 96 is pivoted upwardly and is brought to rest within the slot 100 of the support post 88. In this position, the upper surface of the leveling arm defines a line that is at the same level with a leveling mark or line 102 on the calibration chamber 66, as shown in FIG. 5. With the leveling arm positioned as shown in FIGS. 3 and 5, the I. V. pole 12 is shifted laterally and oriented to bring the end of the arm 96 into contact with the mid-thoracic line of the patient. If the leveling arm 96 is high or low in respect to the mid-thoracic line of the patient, the clamp element 14 is loosened by adjusting wing nuts 16 thereby allowing the support table 20 to be raised or lowered to bring the level arm 96 into proper alignment with the mid-thoracic line of the patient. After this has been accomplished, the clamp element 14 may be tightened by means of the wing nuts and thereafter the level mark 102 of the calibration chamber 66 will be at the same level with the mid-thoracic line of the patient.

Before the cannula 70 is inserted into the patient and pressure monitoring is initiated, it is necessary to purge all air from the tubing system and fill the system with sterile fluid, such as 0.9% normal saline. This is accomplished by orienting stopcock 61 to conduct sterile fluid from reservoir 69 through drip chamber 67 and tubing 65 into the transducer diaphragm chamber 44. Stopcock 60 must be oriented to prevent flow into the calibration chamber 66 and allow flow into the transducer diaphragm chamber 44. Stopcock 56 is opened and the protective cap 57 removed to allow escape of air from the transducer diaphragm chamber and entry of sterile fluid thereto. After all of the air has been purged from the transducer diaphragm chamber 44, stopcock 56 is closed and capped. Thereafter, valve 56 will remain closed. With vent valve 86 oriented to allow escape of air from the calibration chamber and valve 63 oriented to allow fluid flow into the calibration chamber, the valve 60 is oriented to conduct sterile fluid from the reservoir 69 through valve 61, valve 60 and tubing 64 into the calibration chamber 66 to bring the fluid level in the calibration chamber up to the level mark 102. If the calibration chamber is inadvertently overfilled, in this process or subsequently, the excess fluid may be removed through valve 63. After filling the calibration chamber 66 to the level mark 102, valve 61 is turned to conduct sterile fluid through valve 68, blood pressure tubing 62, and the cannula 70 purging all air therefrom. Valve 61 is then oriented to prevent further flow of sterile fluid from the reservoir 69. Now all air is purged from the tubing system having taken care throughout to eliminate any air bubbles as the system is filled with sterile fluid.

It is now possible and desirable to zero the pressure monitoring system. Valve 60 is now turned to communicate the calibration chamber 66 with the transducer diaphragm chamber 44. With vent valve 86 oriented to connect the bacteria filter 74 to the atmosphere, and with the calibration chamber filled to the level mark 102, the diaphragm chamber of the transducer dome will be under zero reference pressure. The readout on the screen 50 of the oscilloscope should then fall on the zero mark of the screen. If it fails to do so, the oscilloscope is adjusted until the zero reference pressure signal falls on the zero or base line.

It will then be desirable to check the accuracy of the pressure monitoring system calibration. This is accomplished by orienting vent valve 86 to connect the bacteria filter 74 with the manometer tube 78 and allowing the valve 60 to remain positioned to communicate the calibration chamber 66 with the transducer diaphragm chamber 44. The pumping bulb 82 of the mercury manometer 80 is then manipulated to pump up a calibration pressure within the calibration chamber. Typically, the pressure pumped within the manometer is 250 millimeters of mercury, thereby pressurizing the transducer diaphragm chamber 44 with a pressure of 250 millimeters of mercury above the zero reference pressure. The strain gauge system of the transducer 38 then develops an electrical signal that is conducted via conductor 46 to the oscilloscope 48, thus producing a pressure indication on the screen of the oscilloscope. This pressure indication should touch the 250 millimeter mark on the oscilloscope screen. If it fails to do so, the oscilloscope is adjusted to bring the indication to the 250 millimeter mark on the oscilloscope screen. If this adjustment is not possible or the oscilloscope is of the type which can not be adjusted, some part of the pressure monitoring system is defective and the defective part must be isolated and replaced.

Since the pressure monitoring system is now purged of air, filled with sterile fluid and properly zeroed and calibrated, stopcock 68 is closed and cannula 70 is inserted into the cardiovascular system of the patient. Valve 60 is then positioned to communicate pressure from the patient into the transducer diaphragm chamber 44. The valve 68 is opened after proper positioning of valve 60, thus communicating the blood pressure of the patient into the diaphragm chamber 44. The level of the fluid-air interface in the calibration chamber may be adjusted by the method previously described using the leveling arm on the transducer support table to be the same as the patient's mid-thoracic level either before or after the procedure of zeroing and calibrating. In any event, in order for accurate blood pressure measurements to be obtained, the level of the fluid-air interface must be maintained at the patient's mid-thoracic level. If, during the monitoring procedure, the level of the patient is changed, it is only necessary to readjust the level of the transducer support table by the method previously described using the leveling arm to restore the accuracy of the pressure measurement system. Rezeroing and recalibrating of the pressure monitoring system are not required.

By employing the above method and apparatus for zeroing and checking calibration of the pressure monitoring system, the physician is assured that the blood pressure waveform appearing on the screen of the oscilloscope is an accurate representation of the patient's blood pressure. Under circumstances where low blood pressure is expected, for example, pulmonary wedge pressure, which is in the order of 6–12 millimeters of mercury, the physician is ensured that the oscilloscope waveform reading is accurate. Further, since the fluid-air interface in the calibration chamber was positively oriented with respect to the mid-thoracic line of the patient, the physician is also assured that no hydrostatic pressure differential exists and, therefore, the oscilloscope waveform presentation accurately represents the blood pressure of the patient.

Figure 6:
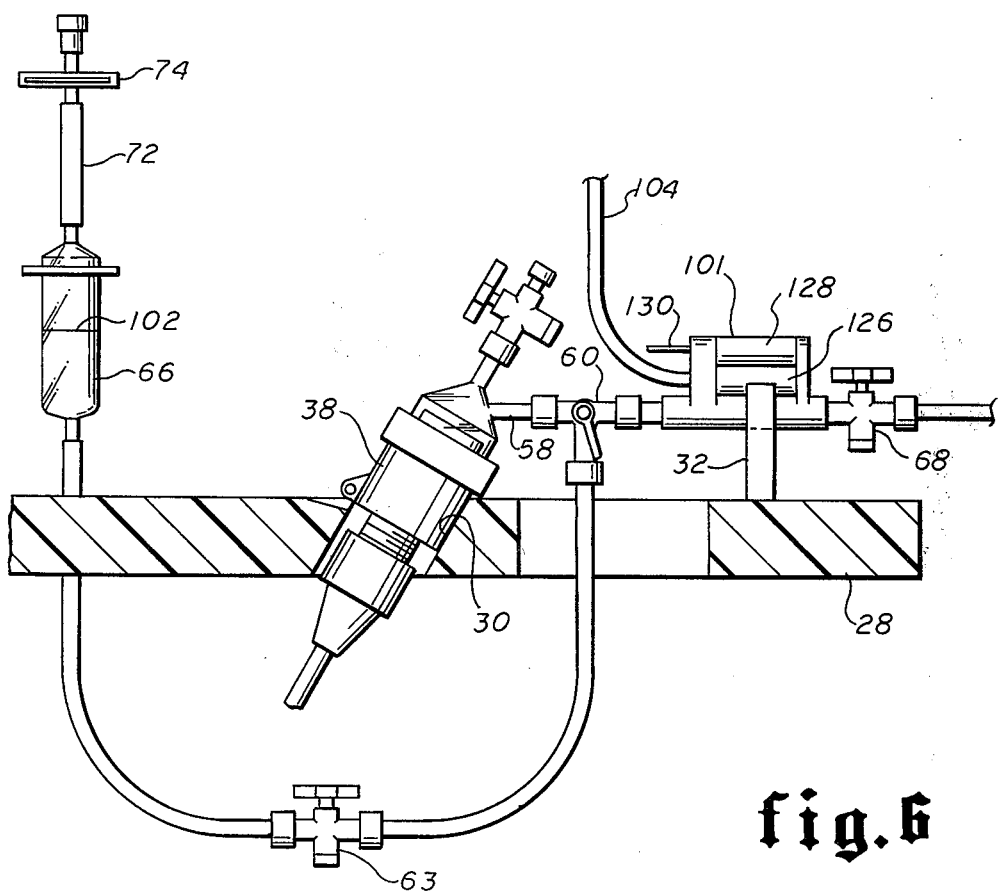
FIG. 6 is a side elevational view of the transducer support structure of the present invention, illustrating a blood pressure monitoring transducer and continuous flush system being supported in protected relation thereby.

The transducer support table 20 is formed to define an arcuate slot 91 within which is secured an arcuate support element 93 having slotted calibration support elements 95 and 97 interconnected therewith. The slots of elements 95 and 97 are oriented in angled relation to one another and receive and securely hold the connector element 72 to properly support the calibration chamber 66 in protected assembly with the support table 20 with the level mark 102 properly leveled with respect to the leveling arm 96 as shown in FIG. 5. The level mark 102 may be at the same level as the transducer dome side connector 58 as shown in FIG. 1 or the level mark 102 may be a different level as shown in FIG. 6. In either case, the method of zeroing and calibrating is the same and the accuracy and other advantages of the method are unaltered.

Figure 2:
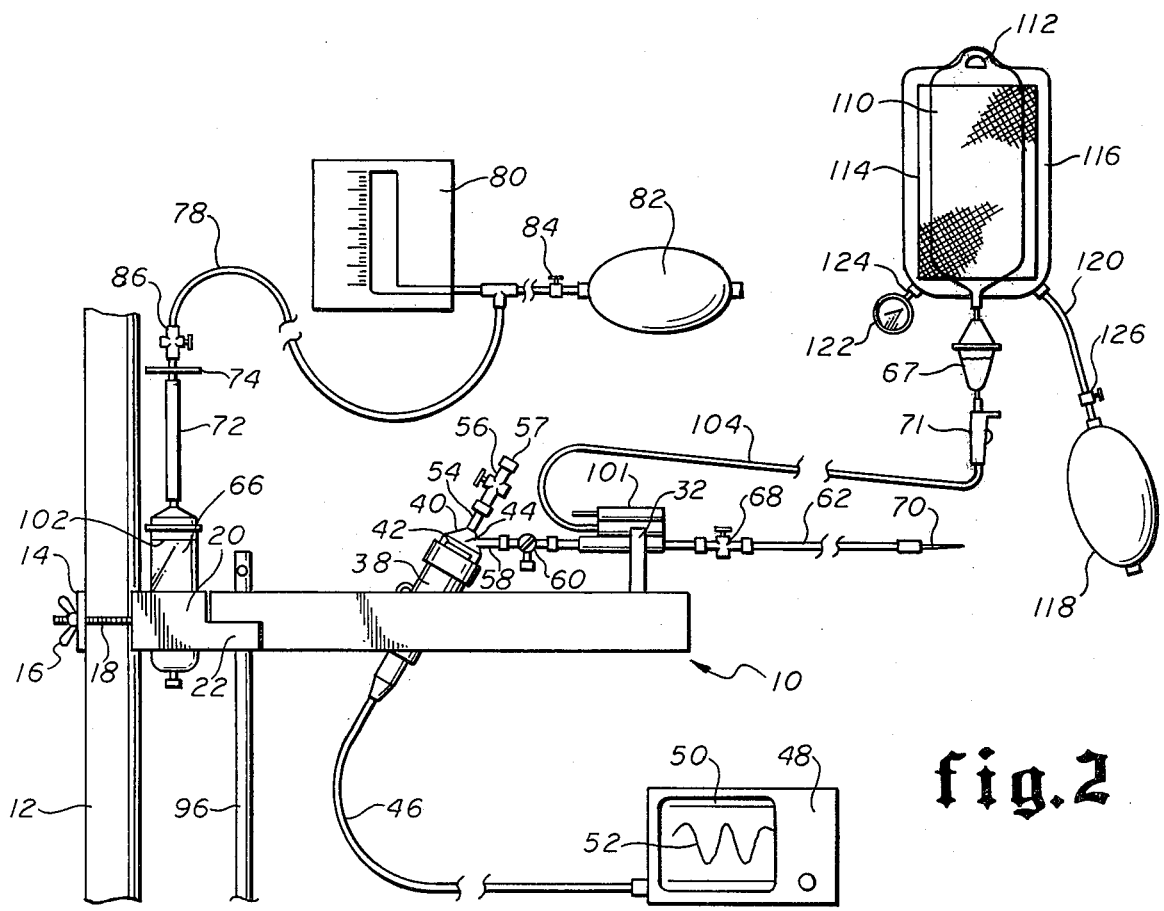
FIG. 2 is a side view of the mechanism similar to that of FIG. 1 and illustrating support of both a transducer and a continuous flush system with transducer zeroing and calibration structure illustrated in partially schematic form.

Although FIG. 1 represents an invasive blood pressure monitoring system of simple form, in most cases, it is desirable to employ a continuous flush system in conjunction with blood pressure monitoring in order to ensure against the development of a thrombus that might cause blockage of the catheter, thereby resulting in an erroneous blood pressure reading on the screen of the oscilloscope. FIG. 2 differs from FIG. 1 in that the blood pressure monitoring system is provided with a continuous flush system that delivers a constant flow of a sterile saline solution which prevents the development of a thrombus or an aggregate of blood on the tip of the catheter and therefore precludes any pressure transmission interference that might otherwise be developed. A continuous flow device 101 is interconnected in communication with the valve 60 and with the catheter control valve 68. A pressurized saline solution tube 104 is interconnected with the continuous flow system 101 and receives pressurized saline solution from a drip chamber 67 through a valve 71 that functions to squeeze the tube 104 in the event flow is to be terminated. The drip chamber 67 is in communication with a flexible container 110 having therein a quantity of sterile 0.9% normal saline solution which may also incorporate an anticoagulant such as heparin. The flexible and collapsible dispensing chamber 110 is provided with a loop 112 at the upper extremity thereof, adapting the flexible container to be supported from the hanger portion of an I. V. stand. The flexible and collapsible container is adapted to be received within a pressure infuser receptacle 114 having a chamber 116 that may be pressurized by means of a bulb pump 118 that is interconnected with chamber 116 by means of a pressure tubing 120. As the pressure chamber 116 is pressurized, pressure is transmitted to the flexible and collapsible container 110 and this pressure is thus transmitted to the saline solution therein. A pressure indicator 122 such as a pressure gauge or mercury manometer may be interconnected by means of a conduit 124 with the pressure chamber 116. Thus, by manipulating the pressure bulb 118, the saline solution within the container 110 may be suitably pressurized and a control valve 126 may be utilized to maintain the saline solution under pressure.

As illustrated in FIG. 6, the continuous flush device 101 includes a restrictor chamber 126 and a fast flush chamber 128. Within the restrictor chamber 126 is provided a restriction device that allows a minute continuous flow of saline solution into the blood pressure monitoring system and thus provides continuous flushing of the catheter to prevent the development of a thrombus thereon which might otherwise cause blockage of the catheter as described above. The continuous flow device is constructed such that a constant flush in the order of 3 cc's per hour of saline solution flow occurs at the tip of the catheter, thus continuously flushing the catheter. This constant flow is sufficiently small that it does not in any way distort the blood pressure waveform that is transmitted by the transducer to the screen of the oscilloscope. The flow through the restrictor is so minute that there is no discernible alteration of the waveform presented on the oscilloscope and the physician will be confident that the blood pressure reading of the oscilloscope screen will be accurate. The pressure chamber 116 is maintained at a pressure of about 300 millimeters of mercury, thus developing sufficient pressure within the dispensing chamber 110, the tube 104, and the restrictor chamber 126 to develop a flow in the order of 3 cc per hour into the blood pressure monitoring system. The fast flush chamber 128 incorporates a valve therein that is opened when a pulling force is applied to a valve actuator element 130. Because of the constant flush system, the tubing and cannula interconnecting the blood pressure monitoring system to the patient will remain patent so that it is not necessary for a nurse or other attendant to periodically flush the system in order to keep it patent.

As mentioned above, continuous flush systems such as shown at 101 in FIG. 6, are well known in the art. One problem with these systems, however, is that they are typically exposed and unprotected and therefore are readily damaged by personnel and equipment movement in the vicinity of the patient. As shown in FIG. 6, the continuous flush device 101, because of the unique transducer support insert structure 28, is shown to rest in protected but accessible manner within the recess of the protective cradle 32. At the same time, the transducer device 38 is also protected since it rests in properly oriented manner within the transducer receptacle 30.

To accomplish zeroing and calibration of the continuous flow-type blood pressure monitoring system of FIGS. 2 and 6, the system is first purged of air. This is accomplished by first turning off the stopcock 68. Stopcock 60 must be oriented to prevent flow into the calibration chamber 66 and allow flow into the transducer diaphragm chamber 44. Stopcock 56 is opened and the protective cap 57 removed to allow escape of air from the transducer diaphragm chamber and entry of sterile fluid thereto. Thereafter, the fast flush valve actuator element 130 on the continuous flow system is manipulated so as to cause the saline solution from the tube 104 to bypass the flow restrictor and enter the transducer diaphragm chamber 44. After all the air has been purged from the transducer diaphragm chamber 44, stopcock 56 is closed and capped. Thereafter, valve 56 will remain closed. With the vent valve 86 oriented to allow escape of air from the calibration chamber and valve 63 oriented to allow fluid flow to the calibration chamber, the valve 60 is then oriented to communicate fluid from the continuous flow device 101 to the calibration chamber 66. The fast flush valve actuator 130 is then manipulated so as to cause saline solution from the tube 104 to bypass the flow restrictor 126 thus filling the calibration chamber to the level mark 102. If the calibration chamber is inadvertently overfilled, in this process or subsequently, the excess fluid may be removed through valve 63. Valve 60 is now turned to prevent further flow to the calibration chamber. Following this, valve 68 is turned on and the fast flush valve actuator 130 is manipulated so as to cause saline solution from the tube 104 to flow through stopcock 68, blood pressure tubing 62, and the cannula 70 purging all air therefrom. Now all air is purged from the tubing system having taken care throughout to eliminate any air bubbles as the system is filled with sterile fluid.

Zeroing of the transducer output signal with respect to the oscilloscope 48 is accomplished by orienting the valve 60 for communication of the calibration chamber 66 with the transducer chamber 44. This valve orientation simultaneously occludes communication between the diaphragm chamber 44 and the cardiovascular system of the patient, even under circumstances where the stopcock 68 is inadvertently allowed to remain open. Atmospheric pressure enters the calibration chamber 66 through valve 86 and the bacteria filter 74, thus ensuring that bacteria and other contaminants do not enter the calibration chamber 66. Zero reference pressure communicated to the diaphragm 42 of the transducer then causes the transducer to generate an electrical signal that is represented on the screen 50 of the oscilloscope as a baseline or zero mark representing atmospheric pressure. The oscilloscope is then adjusted to cause the zero mark to become registered with the base or zero line of the oscilloscope screen.

For calibration, the valve 86 is oriented to communicate the manometer 80 with the calibration chamber 66 and the manometer is then pressurized to apply a preselected calibrating pressure to the liquid column within the calibration chamber 66. The manometer forces air under pressure through the bacteria filter 74 into the calibration chamber thereby pressurizing the air space within the calibration chamber above the fluid to the preselected calibrating pressure, for example, 250 millimeters of mercury. The transducer sensing diaphragm is thereby subjected to a pressure of 250 millimeters of mercury above the zero reference pressure which is communicated to the diaphragm chamber 44 through the tube 64 and the valve 60. This pressure causes a deflection of the trace on the oscilloscope such that that trace is now in registry with the 250 millimeters of mercury line on the face of the oscilloscope. If the trace fails to register with the 250 millimeters of mercury mark, the oscilloscope is adjusted to bring the indication to the 250 millimeters of mercury mark on the oscilloscope screen. If this adjustment is not possible or if the oscilloscope is of the type which cannot be adjusted, some part of the pressure monitoring system is defective and the defective part must be isolated and replaced.

The bacteria filter functions to prevent introduction of any bacteria or other contaminants into the calibration chamber while zeroing and calibrating the pressure monitoring system. The blood pressure monitoring system is thus closed with respect to bacteria and other contaminants even though it is open to the atmosphere across the bacteria filter during zeroing and calibration.

Figure 7:
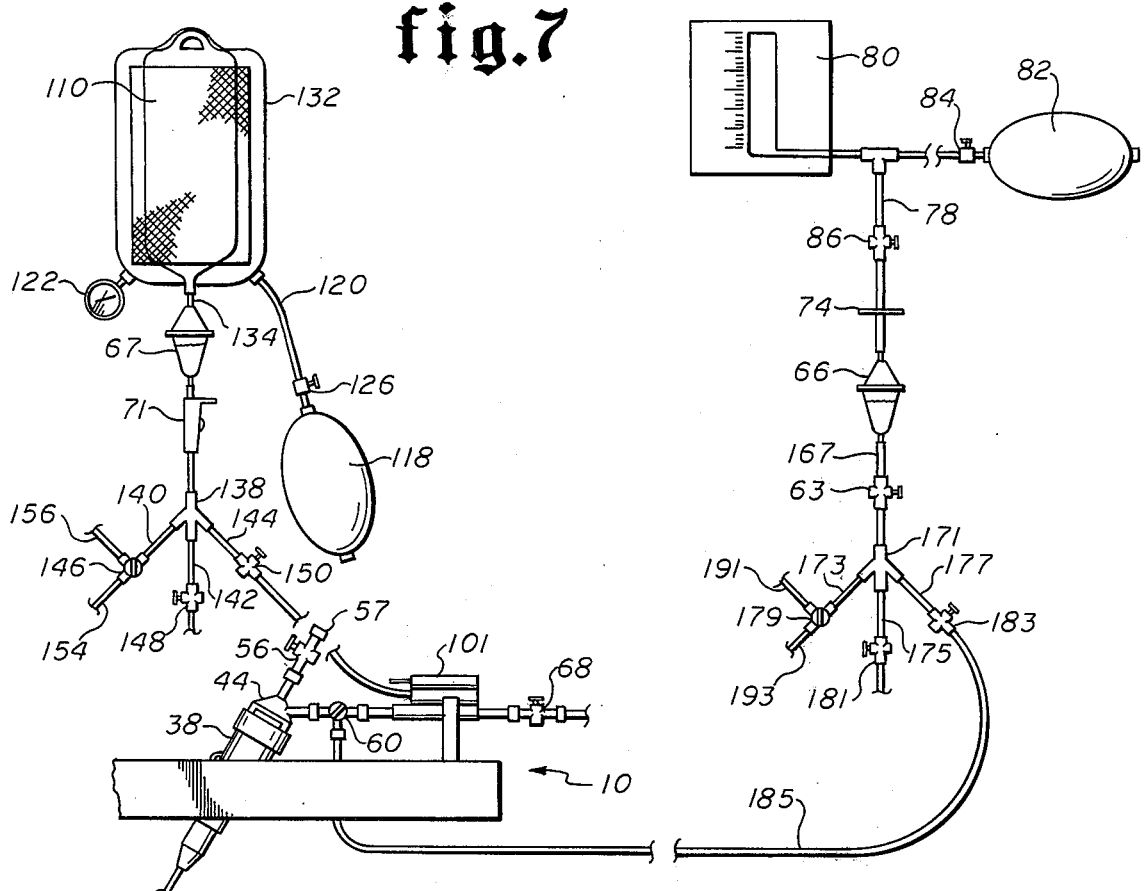
FIG. 7 is a partial side elevational view of the transducer support structure, zeroing and calibrating system, and plumbing system of FIG. 2 and illustrating interconnection of a plurality of blood pressure monitoring systems each with a continuous flush system in order that blood pressure at various points in the cardiovascular system of the patient may be selectively monitored.

As shown in FIG. 7, it is possible to employ a plurality of transducers and catheters for continuous invasive blood pressure monitoring, with each blood pressure monitoring system being provided with a continuous flush system. In this case, as shown in FIG. 7, a single flexible container may be employed as shown at 110 which is positioned within a pressure infuser 132 of the same nature as illustrated in FIG. 2 which pressurizes the saline solution contained within the flexible container 110. An outlet tube 134 extending from the flexible container 110 conducts saline solution from the container to a drip chamber 67 through a roller clamp or valve 71 to a multiple outlet fitting 138 interconnected therewith. As shown, the outlet fitting 138 is of the triple outlet type, having three delivery tubes 140, 142 and 144 extending therefrom. The respective delivery tubes are provided with control valves 146, 148 and 150 that control transmission of the saline solution to individual continuous flush devices such as shown generally at 101. Although valves 148 and 150 are simple on/off stopcock type valves, valve 146 is a four-way selector valve enabling the selection of one or both of a pair of delivery conduits 154 and 156. Thus, a single supply of saline solution may be employed in conjunction with a blood pressure monitoring system including a plurality of transducers that may be interconnected at a plurality of points of the patient's cardiovascular system in order to provide an accurate oscilloscope display of the blood pressure at each of these plurality of points.

Also as shown in FIG. 7, a single calibration chamber 66 with bacteria filter 74 and control valve 86 similar to that in FIGS. 1 and 2 may be connected through tubing 167 and three-way stopcock 63 to another multiple outlet fitting 171. This multiple outlet fitting 171 also has three delivery tubes 173, 175 and 177 extending therefrom. These respective delivery tubes are provided with control valves 179, 181 and 183. Although valves 181 and 183 are simple on/off stopcock valves, valve 179 is a four-way selector valve enabling the selection of one or both of a pair of conduits 191 and 193 extending therefrom. Each of these control valves is connected through tubing such as is shown generally at 185 to a three-way control valve, such as 60, which is interconnected between a transducer diaphragm chamber 44 and a constant infusion device 101. Each of the pressure monitoring systems may be zeroed and calibrated through the bacteria filter 74 and calibration chamber 66 using the mercury manometer 80, pump bulb 82 and control valve 84 by the method previously described. Each pressure monitoring system may be selectively zeroed and calibrated or any number can be zeroed and calibrated simultaneously without contamination of any of the fluid systems or interruption of the operation of any of those not being zeroed or calibrated. Thus, a single calibration chamber with bacteria filter may be employed in zeroing and calibrating in conjunction with a blood pressure monitoring system including a plurality of transducers that may be interconnected at a plurality of points of the patient's cardiovascular system in order to provide an accurate oscilloscope display of the blood pressure at each of these plurality of points. Furthermore, with each of these plurality of transducers with its continuous flush system held and protected in its own transducer support insert all of which are inserted into one transducer support table, the transducer support table may be accurately leveled to the patient's mid-thoracic line by the method previously described using the leveling arm on the transducer support table and thereby eliminating any hydrostatic pressure measurement error from any of the plurality of pressure measurements. Further, each of the plurality of transducers may be of like or different design and each different design being held in its own characteristic transducer support insert will be appropriately leveled with the patient's mid-thoracic line through leveling of the transducer support table and thus the fluid-air interface in the calibration chamber regardless of the actual level of the transducer sensing diaphragm.

Figure 8:
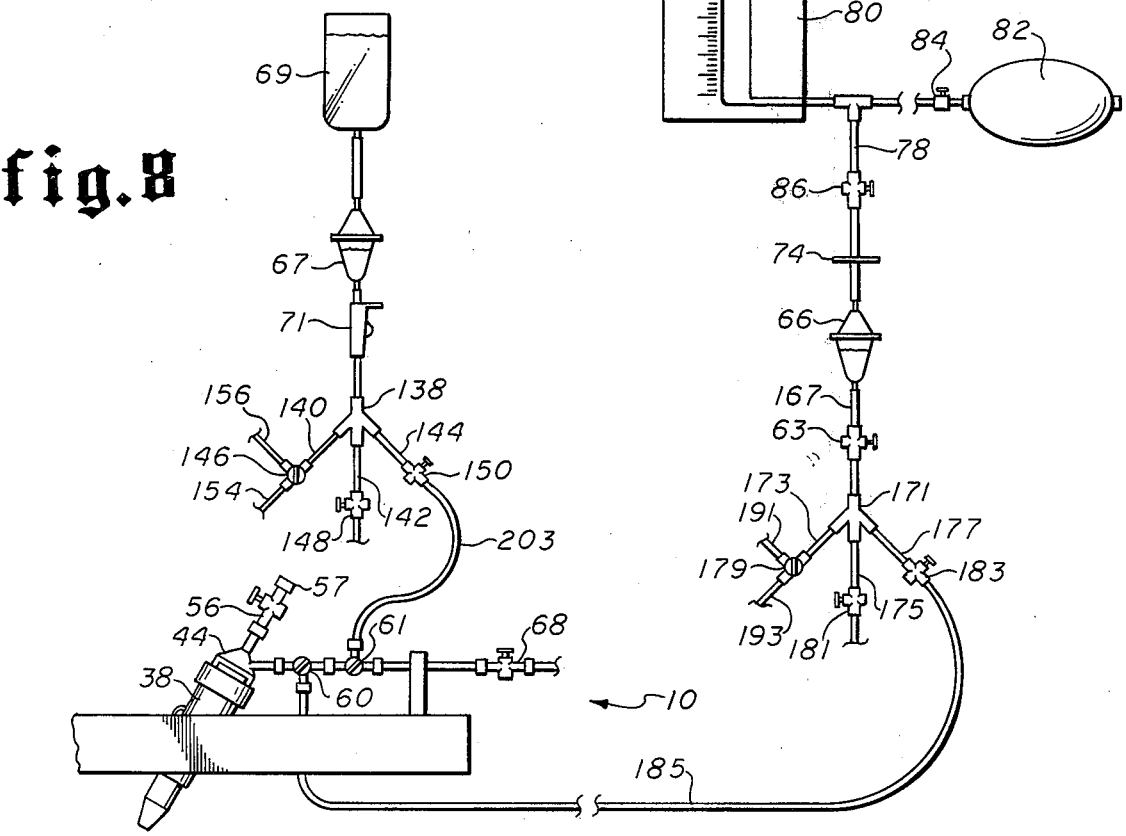
FIG. 8 is a partial side elevational view of the transducer support structure, zeroing and calibrating system, and plumbing system of FIG. 1 and illustrating interconnection of a plurality of blood pressure monitoring systems but without the use of continuous flush systems.

The physician is therefore enabled to simultaneously monitor such pressures in the patient's cardiovascular system such as radial artery pressure, femoral artery pressure, central venous pressure, pulmonary wedge pressure, left atrial pressure, ventricular pressure, etc. In each case, a continuous flush system may be employed to maintain the patentcy of the system and, in each case, a system is employed to positively prevent any possibility of injection of bacteria or other contaminents to the patient during calibration and zeroing. Also, in each case, the transducer may be periodically zeroed and calibrated, if desirable, without in any way altering the closed integrity of the system. The blood pressure monitoring system is effectively maintained in sterile condition at all times and the possibility of introducing bacteria and other contaminants to the patient is therefore eliminated. As shown in FIG. 8, it is also possible to employ a plurality of transducers and catheters for continuous invasive blood pressure monitoring without the use of continuous flush systems. In this case, as shown in FIG. 8, all of the blood pressure monitoring systems are interconnected with one calibration chamber and bacteria filter by the same method as in FIG. 7. However, in this case, a single fluid reservoir 69 is interconnected to a multiple outlet device 138 through a drip chamber 67 and valve 71. The outlet tubes 140, 142 and 144 from the multiple outlet device 138 are provided with control valve 146, 148 and 150, respectively, that control transmission of saline solution to individual blood pressure monitoring systems through a tube and three-way stopcock valve as shown genreally at 203 and 61, respectively. Thus, a single supply of saline solution may be employed in conjunction with a blood pressure monitoring system including a plurality of transducers for the purpose of priming the system with sterile saline solution and purging all air from the system by the method previously described for the illustration in FIG. 1. With the system of FIG. 8, all of the characteristics and features of the system of FIG. 7 for leveling, zeroing and calibrating with a single transducer support table and calibration chamber and bacteria filter are obtained.

In the preferred embodiments as illustrated in FIGS. 7 and 8, a plurality of transducers up to four may be employed. It should be clear that by utilizaton of an appropriate multiple outlet device interconnected with appropriate valves, systems employing either more or fewer transducers may be realized and that for any such system any number of transducers up to the maximum capacity may be used.

Having thus described my invention in detail, I claim:

1. A method of zeroing and calibrating an invasive blood pressure monitoring system with a display device of which an oscilloscope waveform readout is typical and wherein said blood pressure monitoring system incorporates a calibration chamber, a blood pressure transducer having a diaphragm chamber adapted for selective communication with said calibration chamber and, a continuous flushing system is interconnected with said blood pressure monitoring system and continuously flushes the cannula to prevent development of a thrombosis therein, said continuous flushing system functions continuously during said zeroing and calibrating of said blood pressure monitoring system, said method comprising:

purging air from said blood pressure monitoring system and filling the system with sterile fluid including filling the calibration chamber to a predetermined level;

interconnecting the blood pressure transducer with the cardiovascular system of the patient through fluid filled tubing and a cannula inserted into the patient's cardiovascular system;

locating the fluid-air interface in the calibration chamber at the level of the right atrium of the patient's heart;

exposing the diaphragm of said transducer to zero reference pressure while maintaining the closed sterile integrity of said blood pressure monitoring system and setting the oscilloscope such that a zero read-out is indicated;

applying a known desired pressure above the zero reference pressure to said diaphragm and inspecting proper calibration of the pressure monitoring system by inspecting the oscilloscope readout of said known pressure, said known desired pressure above the zero reference pressure being applied to said diaphragm while maintaining the closed sterile integrity of said blood pressure monitoring system;

removing said known desired pressure above the zero reference pressure from said diaphragm after inspection of calibration of the pressure monitoring system is completed; and thereafter applying the cardiovascular pressure of the patient to said diaphragm by communicating said cannula with said diaphragm, thus causing said transducer to transmit an electrical waveform signal to said oscilloscope that is displayed on the screen of said oscilloscope.

2. The method of claim 1, including:
periodically inspecting the zero and calibration of said pressure monitoring system while maintaining said system closed with respect to bacteria and other contaminants.

3. The method of claim 1, wherein:
atmospheric pressure and a known pressure are introduced into said blood pressure monitoring system through a bacteria filter that maintains said closed sterile integrity of said blood pressure monitoring system with respect to bacteria and other contaminants.

4. The method of claim 1, wherein:
establishment of fluid circuitry for inspection of the zero and calibration of said blood pressure monitoring system automatically shuts off communication of the cardiovascular system of the patient with said blood pressure monitoring system, thus providing positive protection against introduction of air emboli to the cardiovascular system of the patient or loss of blood from the cardiovascular system of the patient.

5. The method of claim 1, including:
positioning the fluid-air interface within the calibration chamber at the same level with the right atrium of the patient's heart which is typically the mid-thoracic level of the patient when supine, such proper positioning assuring that no error will be introduced into the pressure measurement due to inaccurate leveling.

6. The method of claim 1, wherein:
the blood pressure monitoring system incorporates a plurality of blood pressure transducers each having a diaphragm chamber adapted for selective communication with a single calibration chamber and each pressure transducer being interconnected through a cannula to a different point in the patient's cardiovascular system.

7. The method of claim 5, wherein said positioning is accomplished by:
positioning a leveling rod in horizontal position and in precise alignment with the fluid-air interface in said calibration chamber; and
bringing the tip of said leveling rod in substantial contact with a point indicating the mid-thoracic line of the patient.

8. A transducer support structure for providing protective support for the transducer and other apparatus of an invasive type blood pressure monitoring system incorporating a calibration chamber and bacteria filter, said support structure comprising:
a transducer support body adapted for positionable interconnection with the upright pole of an I.V. stand;
leveling means being interconnected with said transducer support body and adapted to be positioned for substantial contact with a point defining the mid-thoracic line of the patient, said leveling means defining a level reference;
insert receiver means being provided on said transducer support body;
transducer support insert means being receivable by said insert receiver means, said transducer support insert means defining at least one protective receptacle for a blood pressure monitoring transducer of a particular design; and
a calibration chamber support being interconnected with said transducer support and adapted to position and securely hold a bacteria filter and a calibration chamber with the liquid level mark of the calibration chamber in level registry with said level reference.

9. A transducer support structure as recited in claim 8, wherein:
said transducer support insert means defines a support structure adapted to receive and provide protective support for a continuous flow device interconnected with the transducer dome of said transducer.

10. A transducer support structure as recited in claim 8 wherein said insert receiver means comprises:
an insert support structure being formed to define insert connector receiver means;
mating insert connector means being provided on said transducer support insert means and adapted to establish firm supporting and supported interconnection between said transducer support body and said transducer insert means.

11. A transducer support structure as recited in claim 10, wherein:
said connector receiver means is defined by a plurality of receiver apertures;
said transducer support insert connector means is defined by a plurality of connector pins extending from said transducer support insert means and adapted to be received within said receiver apertures.

12. A transducer support structure as recited in claim 10, wherein said insert connector receiver means and mating insert connector means are so located and said transducer support inserts are so formed as to provide a channel between the transducer support structure body and adjacent transducer support insert and between adjacent transducer support inserts.

13. A transducer support structure as recited in claim 8, wherein said leveling means comprises:
a level support projecting from said support body;
a level arm receiver projecting from said support body in spaced relation with said level support; and
a level arm being pivotally interconnected with said level support and adapted for supported engagement with said level arm receiver to position said level arm in level position and establish said level reference.

14. A transducer support structure as recited in claim 8, wherein said transducer support insert means comprises:
an insert body being formed to define a transducer receptacle, such that said transducer receptacle fits the body design of a particular transducer and orients said transducer in angulated relation with said level reference and thereby orients the side port of the transducer dome in parallel horizontal relation with said level reference.

15. A transducer support structure as recited in claim 14, wherein said transducer support insert means further comprises:
a support receiver projecting from said insert body in spaced relation with said transducer receptacle, said support receiver adapted to provide protective support for a continuous flush device interconnected with said side port of said transducer.

16. A transducer support structure as recited in claim 14, wherein said transducer support insert means further comprises:
a recess to which tubing may be passed through said channel and through which said tubing may extend downward through said transducer support insert.

17. A transducer support structure as recited in claim 14, wherein:
said transducer support insert means is further formed to define a channel between the recess and the transducer receptacle to provide for passage of a transducer electrical cable through said channel to allow positioning of said transducer in said transducer receptacle without disconnecting said transducer electrical cable from said transducer and an oscilliscope to which said transducer electrical cable is also connected.

18. Apparatus for zeroing and calibrating an invasive cardiovascular hemodynamic monitoring system, said apparatus including:
a calibration chamber interconnected with a bacteria filter, said bacteria filter ensuring that no bacteria or other contaminants are allowed to pass into the calibration chamber from the external environment during the process of zeroing and calibrating the blood pressure monitoring system, thereby protecting the cardiovascular system of the patient from bacterial contamination from the blood pressure monitoring system;

a selector valve having a first connector assembled to the pressure receiver inlet connector of a blood pressure transducer, a second connector interconnected with a cannula tube located in the patient's cardiovascular system and a third connector being interconnected with said calibration chamber, said selector valve being positionable at a monitoring position communicating the blood pressure of the patient to the diaphragm chamber of the blood pressure transducer and blocking communication between the patient and said calibration chamber, said valve being positionable at a calibration position communicating said calibration chamber with said diaphragm chamber and blocking communication between the patient and both said calibration chamber and said diaphragm chamber, the patient thus being protected by said valve against inadvertent injection of air emboli or loss of blood both during zeroing and calibration of the blood pressure monitoring system, said valve being positionable at a purging position communicating said calibration chamber with a source of sterile fluid for filling the calibration chamber to the proper level mark.

19. A method of zeroing and calibrating an invasive blood pressure monitoring system with a display device of which an oscilloscope waveform readout is typical and wherein said blood pressure monitoring system incorporates a calibration chamber and a plurality of blood pressure transducers each having a diaphragm chamber adapted for selective communication with a calibration chamber, said method comprising:

purging air from said blood pressure monitoring system and filling the system with sterile fluid including filling the calibration chamber to a predetermined level;

interconnecting the blood pressure transducers with the cardiovascular system of the patient through fluid filled tubing and a cannula inserted into the patient's cardiovascular system;

locating the fluid-air interface in the calibration chamber at the level of the right atrium to the patient's heart;

exposing the diaphragm of said transducer to zero reference pressure while maintaining the closed sterile integrity of said blood pressure monitoring system and setting the oscilloscope such that a read-out is indicated;

applying a known desired pressure above the zero reference pressure to said diaphragm and inspecting proper calibration of the pressure monitoring system by inspecting the oscilloscope readout of said known pressure, said known desired pressure above the zero reference pressure being applied to said diaphragm while maintaining the closed sterile integrity of said blood pressure monitoring system;

removing said known desired pressure above the zero reference pressure from said diaphragm after inspection of calibration of the pressure monitoring system is completed;

and thereafter applying the cardiovascular pressure of the patient to said diaphragms by communicating said cannula with said diaphragms, thus causing said transducer to transmit an electrical waveform signal to said oscilloscope that is displayed on the screen of said oscilloscope.

20. The method of claim 19, including:
periodically inspecting the zero and calibration of said pressure monitoring system while maintaining said system closed with respect to bacteria and other contaminants.

21. The method of claim 19, wherein:
atmospheric pressure and a known pressure are introduced into said blood pressure monitoring system through a bacteria filter that maintains said closed sterile integrity of said blood pressure monitoring system with respect to bacteria and other contaminants.

22. The method of claim 19, wherein:
establishment of fluid circuitry for inspection of the zero and calibration of said blood pressure monitoring system automatically shuts off communication of the cardiovascular system of the patient with said blood pressure monitoring system, thus providing positive protection against introduction of air emboli to the cardiovascular system of the patient or loss of blood from the cardiovascular system of the patient.

23. The method of claim 19, wherein:
a continuous flushing system is interconnected with said blood pressure monitoring system and continuously flushes the cannula to prevent development of a thrombus thereon, said continuous flushing system functions continuously during said zeroing and calibrating of said blood pressure monitoring system.

24. The method of claim 19, including:
positioning the fluid-air interface within the calibration chamber at the same level with the right atrium of the patient's heart which is typically the mid-thoracic level of the patient when supine, such proper positioning assuring that no error will be introduced into the pressure measurement due to inaccurate leveling.

25. The method of claim 24, wherein said positioning is accomplished by:
positioning a leveling rod in horizontal position and in precise alignment with the fluid-air interface in said calibration chamber; and
bringing the tip of said leveling rod in substantial contact with a point indicating the mid-thoracic line of the patient.

26. Apparatus for zeroing and calibrating an invasive cardiovascular hemodynamic monitoring system, said apparatus including:

a calibration chamber interconnected with a bacteria filter, said bacteria filter ensuring that no bacteria or other contaminants are allowed to pass into the calibration chamber from the external environment during the process of zeroing and calibrating the blood pressure monitoring system, thereby protecting the cardiovascular system of the patient from bacterial contamination from the blood pressure monitoring system;

a plurality of selector valves having a first connector assembled to the pressure receiver inlet connector of a blood pressure transducer, a second connector interconnected with a cannula tube located in the patient's cardiovascular system and a third connector being interconnected with said calibration chamber, each said selector valves being positionable at a monitoring position communicating the blood pressure of the patient to the diaphragm chamber of the blood pressure transducer and blocking communication between the patient and said calibration chamber, said valves being positionable at a calibration position communicating said calibration chamber with said diaphragm chamber and blocking communication between the patient and both said calibration chamber and said diaphragm chamber, the patient thus being protected by said valve against inadvertent injection of air emboli or loss of blood both during zeroing and calibration of the blood pressure monitoring system, said valves being positionable at a purging position communicating said calibration chamber with a source of sterile fluid for filling the calibration chamber to the proper level mark, each said selector valve being independently positionable for monitoring, calibrating, and purging.

* * * * *